US011850243B2

(12) United States Patent
Nguyen et al.

(10) Patent No.: US 11,850,243 B2
(45) Date of Patent: Dec. 26, 2023

(54) DIHYDROPYRIDINE COMPOSITIONS AND METHODS FOR TREATING NEUROLOGICAL DISORDERS

(71) Applicants: Cavalon Therapeutics, Inc., Berkeley, CA (US); Northwestern University, Evanston, IL (US)

(72) Inventors: Jack Nguyen, Berkeley, CA (US); Dalton James Surmeier, Jr., Chicago, IL (US)

(73) Assignees: Northwestern University, Evanston, IL (US); Cavalon Therapeutics, Inc., Berkeley, CA (US)

( * ) Notice: Subject to any disclaimer, the term of this patent is extended or adjusted under 35 U.S.C. 154(b) by 0 days.

(21) Appl. No.: 17/574,272

(22) Filed: Jan. 12, 2022

(65) Prior Publication Data

US 2022/0241262 A1 Aug. 4, 2022

Related U.S. Application Data

(60) Provisional application No. 63/136,845, filed on Jan. 13, 2021.

(51) Int. Cl.
*A61K 31/4439* (2006.01)
*A61P 25/16* (2006.01)

(52) U.S. Cl.
CPC .......... *A61K 31/4439* (2013.01); *A61P 25/16* (2018.01)

(58) Field of Classification Search
CPC ................. A61K 31/4433; A61P 25/14–16
See application file for complete search history.

(56) References Cited

U.S. PATENT DOCUMENTS 9,463,186 B2 * 10/2016 Surmeier ........... A61K 31/4439
2020/0323835 A1 10/2020 Surmeier et al.

FOREIGN PATENT DOCUMENTS

WO WO-2022155227 A1 7/2022

OTHER PUBLICATIONS

Johnson et al, Kinetic and cardiovascular comparison of immediate-release isradipine and sustained-release isradipine among non-treatment-seeking, cocaine-dependent individuals, Progress in Neuro-Psychopharmacology and Biological Psychiatry, vol. 29, Issue 1, 2005, pp. 15-20. (Year: 2005).*
Parkinson's Disease Isradipine Safety Study NCT00753636 ([Online], [Retrieved on Jan. 6, 2022], Retrieved from https://www.clinicaltrials.gov/ct2/history/NCT00753636, Jul. 1, 2011 Study Record Version) (Year: 2011).*
Parkinson Study Group, Phase II safety, tolerability, and dose selection study of isradipine as a potential disease-modifying intervention in early Parkinson's disease (STEADY-PD). Mov Disord., 2013. 28: 1823-1831 (Year: 2013).*
Carrara V, Porchet H, Dayer P. Influence of input rates on (+/−)-isradipine haemodynamics and concentration-effect relationship in healthy volunteers. Eur J Clin Pharmacol. 1994;46(1):29-33. doi: 10.1007/BF00195912. PMID: 8005183. (Year: 2019).*
STEADY-PD III Phase III protocol NCT02168842 ([online], [Retrieved on Jan. 6, 2022], Retrieved from https://clinicaltrials.gov/ct2/history/NCT02168842?V_32=View#StudyPageTop, Study Protocol (Prot_000.pdf), uploaded on Nov. 25, 2019) (Year: 2019).*
Anekonda, T.S. et al. (Jan. 2011) L-type voltage-gated calcium channel blockade with isradipine as a therapeutic strategy for Alzheimer's disease. Neurobiol Dis, 41:62-70. NIH Public Access Author Manuscript; 18 pages.
Bean, B.P. (Jun. 2007) The action potential in mammalian central neurons. Nat Rev Neurosci, 8:451-465.
Becker, C. et al. (Feb. 2008) Use of antihypertensives and the risk of Parkinson disease. Neurology, 70:1438-1444.
Berg, D. et al. (Mar. 2014) Time to redefine PD? Introductory statement of the MDS Task Force on the definition of Parkinson's disease. Mov Disord, 29(4):454-462.
Caraveo, G. et al. (Aug. 2014) Calcineurin determines toxic versus beneficial responses to α-synuclein. Proc Natl Acad Sci USA, 111:E3544-3552.
Carrara, V. et al. (1994) Influence of input rates on (±)-isradipine haemodynamics and concentration-effect relationship in healthy volunteers. Eur J Clin Pharmacol, 46:29-33.
clinicaltrials.gov, NCT02168842. A Phase 3 double-blind placebo-controlled parallel group study of isradipine as a disease modifying agent in subjects with early Parkinson disease. First Posted Jun. 20, 2014; Last Update Jan. 14, 2020 [online]. Retrieved from: https://www.clinicaltrials.gov/ProvidedDocs/42/NCT02168842/Prot_000.pdf, 12 pages.
Diederich, N. et al. (Feb. 2019). Parkinson's disease: Is it a consequence of human brain evolution? Mov Disord, 34(4):453-459.
Diepenbroek, M. et al. (Mar. 2014) Overexpression of the calpain-specific inhibitor calpastatin reduces human alpha-synuclein processing, aggregation and synaptic impairment in [A30P]αSyn transgenic mice. Hum Mol Genet, 23(15):3975-3989.
Dufty, B.M. et al. (May 2007) Calpain-cleavage of alpha-synuclein. Connecting proteolytic processing to disease-linked aggregation. Am J Pathol, 170:1725-1738.
Gegg, M.E. and Schapira, A.H.V. (2016) Mitochondrial dysfunction associated with glucocerebrosidase deficiency. Neurobiol Dis, 90:43-50.
Gómez-Sintes, R. et al. (Mar. 2016) Lysosomal cell death mechanisms in aging. Ageing Res Rev, 32:150-168.

(Continued)

*Primary Examiner* — Theodore R. Howell
(74) *Attorney, Agent, or Firm* — COOLEY LLP; Ivor R. Elrifi; Eric A. Owens (57) ABSTRACT

The present disclosure provides extended or sustained release compositions of a dihydropyridine calcium channel blocker, specifically isradipine, and method of using the compositions for the treatment of neurological disorders, wherein the composition provides sustained plasma levels of the dihydropyridine calcium channel blocker.

23 Claims, 1 Drawing Sheet

(56) References Cited

OTHER PUBLICATIONS

Gudala, K. et al. (2015) Reduced risk of Parkinson's disease in users of calcium channel blockers: a meta-analysis. Int J Chronic Dis, 2015: Article ID 697404, 7 pages.
Gupta, A. et al. (Dec. 2008). What causes cell death in Parkinson's disease? Ann Neurol, 64:S3-S15. NIH Public Access Author Manuscript, 22 pages.
Guzman, J.N. et al. (Dec. 2010) Oxidant stress evoked by pacemaking in dopaminergic neurons is attenuated by DJ-1. Nature, 468:696-700. HHS Public Access Author Manuscript, 12 pages.
Guzman, J.N. et al. (2018) Systemic isradipine treatment diminishes calcium-dependent mitochondrial oxidant stress. J Clin Invest, 128:2266-2280.
Hornykiewicz, O. (2002) Dopamine miracle: from brain homogenate to dopamine replacement. Mov Disord 17(3):501-508.
Ilijic, E. et al. (Aug. 2011) The L-type channel antagonist isradipine is neuroprotective in a mouse model of Parkinson's disease. Neurobiol Dis, 43(2):364-371. NIH Public Access Author Manuscript, 14 pages.
Lee, Y.-C. et al. (Jun. 2014) Antihypertensive agents and risk of Parkinson's disease: a nationwide cohort study. PLoS One, 9(6):e98961, http://dx.doi.org/10.1371/journal.pone.0098961, 8 pages.
Llorente-Folch, I. et al. (Mar. 2015) The regulation of neuronal mitochondrial metabolism by calcium. J Physiol Lond 593:3447-3462.
Matsuda, W. et al. (Jan. 2009) Single nigrostriatal dopaminergic neurons form widely spread and highly dense axonal arborizations in the neostriatum. J Neurosci, 29:444-453.
Medina, D.L et al. (Jun. 2015) Lysosomal calcium regulates autophagy. Autophagy, 11:970-971.
Morikawa, H. and Paladini, C.A. (Dec. 2011) Dynamic regulation of midbrain dopamine neuron activity: intrinsic, synaptic, and plasticity mechanisms. Neuroscience, 198:95-111. NIH Public Access Author Manuscript, 29 pages.
Nedergaard, S. et al. (1993) Nifedipine- and omega-conotoxin-sensitive Ca2+ conductances in guinea-pig substantia nigra pars compacta neurones. J Physiol Lond, 466:727-747.
Parkinson Study Group (Sep. 2013). Phase II safety, tolerability, and dose selection study of isradipine as a potential disease-modifying intervention in early Parkinson's disease (STEADY-PD). Mov Disord, 28(13):1823-1831.
Parkinson Study Group (May 2020) Isradipine versus placebo in early Parkinson disease: a randomized trial. Simuni, T. et al. (Contibuting Authors); Ann Inter Med, 172:591-598. HHS Public Access Author Manuscript, 21 pages.
Pasternak, B. et al. (Mar. 2012) Use of calcium channel blockers and Parkinson's disease. Am J Epidemiol, 175:627-635.
Puopolo, M. et al. (Jan. 2007) Roles of subthreshold calcium current and sodium current in spontaneous firing of mouse midbrain dopamine neurons. J Neurosci, 27:645-656.
Rcom-H'Cheo-Gauthier, A. et al. (Aug. 2014) Interactions between calcium and alpha-synuclein in neurodegeneration. Biomol Ther, 4:795-811.
Reeve, A. et al. (2014) Ageing and Parkinson's disease: why is advancing age the biggest risk factor? Ageing Res Rev, 14:19-30.
Ritz, B. et al. (May 2010) L-type calcium channel blockers and Parkinson disease in Denmark. Ann Neurol, 67:600-606. NIH Public Access Author Manuscript, 11 pages.
Sánchez-Padilla, J et al. (Jun. 2014) Mitochondrial oxidant stress in locus coeruleus is regulated by activity and nitric oxide synthase. Nat Neurosci, 17(6):832-840. HHS Public Access Author Manuscript, 26 pages.
Striessnig, J. et al. (Mar. 1998) Structural basis of drug binding to L Ca2+ channels. Trends Pharmacol Sci, 19:108-115.
Surmeier, D.J. et al. (Feb. 2017) Calcium and Parkinson's disease. Biochem Biophys Res Commun, 483:1013-1019. HHS Public Access Author Manuscript, 17 pages.
Surmeier, D.J. et al. (Jan. 2017) Selective neuronal vulnerability in Parkinson disease. Nat Rev Neurosci, 18:101-113. HHS Public Access Author Manuscript, 28 pages.
Venuto, C.S. et al. (Jan. 2021) Isradipine plasma pharmacokinetics and exposure response in early Parkinson's disease Ann Clin Transl Neurol, 8:603-612.
Votyakova, T.V. and Reynolds, I.J. (2001) DeltaPsi(m)-dependent and -independent production of reactive oxygen species by rat brain mitochondria. J Neurochem, 79:266-277.
Wong, E. and Cuervo, A.M. (Jul. 2010) Autophagy gone awry in neurodegenerative diseases. Nat Neurosci 13:805-811. NIH Public Access Author Manuscript, 17 pages.
Christensen et al. "Pharmacokinetics and dynamic response of plain and slow release isradipine formulations in moderately hypertensive patients", Pharmacology & Toxicology, (1993); 73(5):279-284.
International Search Report and Written Opinion for International Application No. PCT/US2022/012154, dated Mar. 30, 2022, 8 pages.
Tse et al. "Pharmacokinetics of PN 200-110 (isradipine), a new calcium antagonist, after oral administration in man", European Journal of Clinical Pharmacology, (1987); 32:361-365.

\* cited by examiner

DIHYDROPYRIDINE COMPOSITIONS AND METHODS FOR TREATING NEUROLOGICAL DISORDERS

CROSS REFERENCE TO RELATED APPLICATIONS

This application claims priority to, and the benefit of, U.S. Provisional Application No. 63/136,845, filed on Jan. 13, 2021, the content of which is incorporated by reference in its entirety.

BACKGROUND OF THE INVENTION

Parkinson's disease (PD) is the most common form of a broad class of movement disorders called parkinsonism defined by the appearance of bradykinesia, rigidity or tremor. The cardinal motor manifestations of clinical PD are attributable to the progressive loss of dopaminergic (DA) neurons in the substantia nigra pars compacta (SNc) that innervate the basal ganglia (Berg et al., 2014; Hornykiewicz, 2002). Several features of these neurons appear to make them selectively vulnerable to factors thought to cause PD, like aging, genetic mutations and environmental toxins. The most notable and best characterized of these features is a long and highly branched axon with a large number of transmitter release sites. This diffuse axonal arbor helps these neurons coordinate the activity in large, distributed basal ganglia networks. SNc DA neuron axons in rodents have as many as 200,000 transmitter release sites and in humans this number rises to over 1M—orders of magnitude more than the vast majority of neurons in the brain (Matsuda et al., 2009; Diederich et al., 2019).

Another shared feature of at-risk neurons appears to be their distinctive physiology. In vivo, at-risk neurons that have been studied have slow tonic activity (Surmeier et al., 2017b). The best studied member of this class is the SNc DA neuron. The action potential of these neurons is slow and broad, which maximizes Ca2+ entry and promotes slow rhythmic activity (Bean, 2007). The slow, rhythmic activity (2-10 Hz) in these neurons is autonomously generated and accompanied by slow oscillations in intracellular Ca2+ concentration that are triggered by the opening of plasma membrane Ca2+ channels with a Cav1.3 pore-forming subunit, which induce the release of Ca2+ from intracellular, endoplasmic reticulum (ER) stores (Guzman et al., 2010; Morikawa and Paladini, 2011; Nedergaard et al., 1993; Puopolo et al., 2007; Guzman et al., 2018).

One consequence of the anatomical and physiological characteristics of at-risk neurons is an elevated bioenergetic demand to support a highly arborized axonal, a vast number of transmitter release sites, intracellular $Ca^{2+}$ oscillations and sustained spike activity. Cav1.3 channels play a critical role in meeting the bioenergetic needs of at-risk neurons by promoting Ca2+ entry into mitochondria, which then acts as a secondary messenger to induce oxidative phosphorylation (OXPHOS) and the production of ATP (Guzman et al., 2010; Llorente-Folch et al., 2015; Sánchez-Padilla et al., 2014). However, induction of OXPHOS also results in the production of reactive oxygen species (ROS) and reactive nitrogen species (RNS) (Goldberg et al., 2012; Guzman et al., 2010; Sánchez-Padilla et al., 2014; Votyakova and Reynolds, 2001). ROS and RNS damage proteins, lipids and DNA, particularly in mitochondria. Sustained oxidant stress could be a major factor underlying declining mitochondrial function in at-risk neurons with age (Reeve et al., 2014). ROS and RNS also can exacerbate the impact of genetic mutations and environmental toxins affecting mitochondria (Gegg and Schapira, 2016), as well as increase the propensity of misfolded alpha-synuclein (aSYN) to aggregate (Gupta et al., 2009), which is a hallmark of cPD. The second downside is that this mechanism results in sustained elevations in cytosolic Ca2+ concentration. Ca2+ promotes aSYN aggregation both directly (Rcom-H'cheo-Gauthier et al., 2014) and indirectly through activation of calpain and calcineurin (Caraveo et al., 2014; Diepenbroek et al., 2014; Dufty et al., 2007). Elevated cytosolic Ca2+ also impairs lysosomal function and turnover of misfolded proteins (Gómez-Sintes et al., 2016; Medina and Ballabio, 2015), potentially synergizing with other defects in proteasomal/autophagic function to increase the likelihood of aSYN accumulation (Wong and Cuervo, 2010).

Thus, $Ca^{2+}$ entry through Cav1.3 channels contributes to both mitochondrial and proteostatic stress in neurons that are at-risk in PD. As a consequence, inhibition of Cav1.3 channels should lower the stress on at-risk neurons and slow PD progression. Dihydropyridines (DHPs) include FDA-approved, selective negative allosteric modulators (NAMs) of Cav1 channels that have good brain bioavailability (Anekonda et al., 2011; Striessnig et al., 1998; Surmeier et al., 2017a). Epidemiological studies have consistently found that the use of DHPs, including isradipine, is associated with a decreased risk of developing PD (Becker et al., 2008; Gudala et al., 2015; Lee et al., 2014; Pasternak et al., 2012; Ritz et al., 2010. Recently, Guzman et al. 2017 demonstrated that chronic inhibition of Cav1.3 channels in vivo with isradipine led to a sustained reduction in cytosolic [Ca2+] in SNc DA neurons, significantly lowered mitochondrial oxidant stress, diminished a high basal rate of mitophagy, and increased mitochondrial mass in SNc DA neurons. Furthermore, in a mouse model of PD (6-hydroxydopamine), systemic administration of isradipine resulted in a concentration-dependent protection of dopaminergic neurons in the striatum and substantia nigra (Ilijic 2011). The plasma concentration required to inhibit neuronal death by 50% ($IC_{50}$) was 5-7 ng/mL, and the threshold plasma concentration for protection against neuronal death (as determined by the inflection point in the concentration-response curve) was approximately 1.5-2 ng/mL. These results correspond well with in vitro data demonstrating that the $IC_{50}$ for inhibition of calcium currents through Cav1.3 by isradipine was approximately 3 ng/mL (Ilijic 2011).

Based on the preclinical and epidemiological data summarized above, two clinical studies were conducted to evaluate the safety and efficacy of isradipine in PD. The primary object of the first study (STEADY-PD II) was to determine the safety and tolerability of isradipine in PD patients (Parkinson Study Group, 2013). Approximately 100 subjects were randomized to placebo or one of 3 dose levels of an extended release (ER) formulation of isradipine (5, 10, or 20 mg/day once daily) for 52 weeks. Based on pre-specified criteria, the 10 mg/day dose of ER isradipine was determined to be the maximum tolerated dose. Subsequently, the efficacy of isradipine in an immediate release (IR) form was evaluated in early stage PD (STEADY-PD III, Parkinson Study Group, 2020). In this study, 336 subjects were randomized to either placebo or 10 mg/day IR isradipine (5 mg BID) for 36 months. The study did not meet its primary objective of change from baseline of the United Parkinson's Disease Rating Scale. Adjusted least-squares mean changes in total UPDRS score in the antiparkinson medication ON state over 36 months for IR isradipine and placebo recipients were 2.99 (95% CI, 0.95 to 5.03) points versus 3.26 (CI, 1.25 to 5.26) points, respectively, with a treatment effect of −0.27 (CI, −3.02 to 2.48) point (P=0.85). The authors concluded that these results do not support the hypothesis that isradipine, at this dose, slows the progression of early-stage PD, and that the dose selected may have been too low to provide the necessary inhibition of the targeted calcium channels.

SUMMARY OF THE INVENTION

The inventors have discovered that the efficacy of isradipine at treating PD is critically dependent on maintaining plasma concentrations above the therapeutic threshold for the majority of the 24-hour day. While multiple parameters may affect the efficacy of isradipine in PD, including dose, the inventors discovered that time above a threshold concentration, as opposed to maximum plasma concentration ($C_{max}$), was the primary pharmacodynamically linked variable. The threshold plasma concentration combined with the time above that concentration provide the surprising effects described herein.

Figure 1:
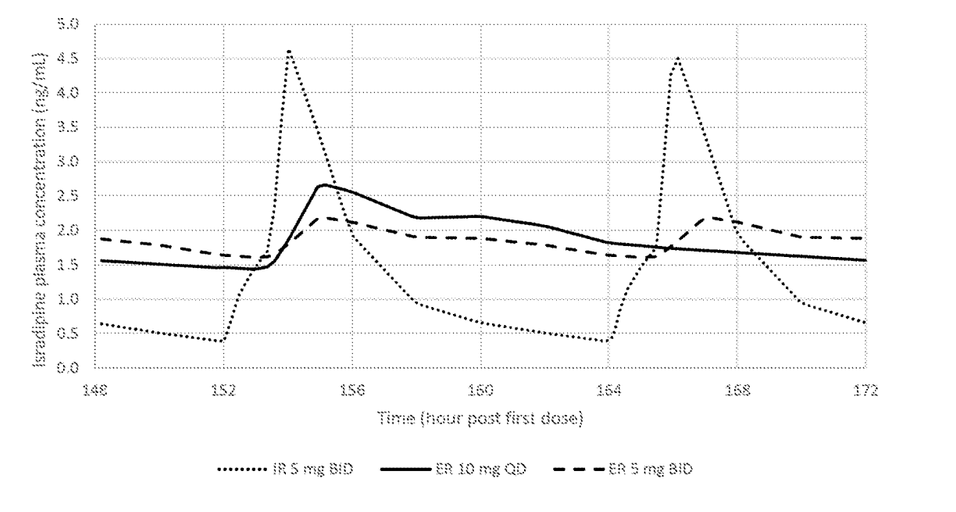
FIG. 1 depicts the steady-state pharmacokinetic profiles of IR isradipine 5 mg BID, ER isradipine 10 mg QD, and ER isradipine 5 mg BID, simulated using non-parametric superposition, based on single dose PK data in healthy volunteers from Carrara 1994.

While STEADY-PD II (described above) was primarily a safety and tolerability study, efficacy measures (UPDRS scores) were collected. Post hoc analyses of these results demonstrated that ER isradipine at the 10 mg/day significantly reduced both total UPDRS scores (motor and non-motor disability) and UPDRS part III scores (motor disability) compared to placebo (Example 1), suggestive that isradipine can delay the progression of PD. These results are in conflict with the results from STEADY-PD III described above, wherein 10 mg/day of IR isradipine did not significantly reduce UPDRS scores compared to placebo. The inventors have discovered that the differences in results between STEADY-PD II and STEADY-PD III may be due to the preparation and administration of isradipine used in each study. To illustrate this point, the steady-state pharmacokinetic profiles for the ER and IR isradipine dosing regimens utilized in STEADY-PD II and III were approximated. As detailed PK data were not available for the exact ER formulation used in STEADY-PD II (DynaCirc CR), steady-state simulations were performed using single dose PK data in healthy volunteers from an alternative ER formulation (Lomir SRO, Example 2, Carrara 1994). As shown in FIG. 1, ER isradipine administered at 10 mg QD produced a relatively flat concentration-time profile with minimal peak-to-trough fluctuations at steady state. On the other hand, IR isradipine administered at 5 mg BID produced a concentration-time profile characterized by sharp peaks and troughs with relatively higher peak-to-trough fluctuations at steady state. Importantly, the steady state PK profile produced by the ER formulation demonstrated that plasma concentrations were maintained near or above the therapeutic threshold (1.5-2 ng/mL, as determined from non-clinical studies described above) for the entirety of the 24-hour day. In contrast, time above threshold at steady state for the IR formulation was limited to approximately 6 hours. Furthermore, it should be noted that, at the same dose, the $C_{max}$ produced by the IR formulation is approximately 2-fold higher than the $C_{max}$ produced by the ER formulation, indicative that the $C_{max}$ is not a primary factor to the efficacy of isradipine for treating PD.

In order to further explore the relationship between PK and efficacy for isradipine, a post-hoc analysis was conducted for the STEADY-PD III data wherein isradipine subjects were divided into three equal groups based on clearance (e.g. slow, medium, or fast clearance). Subjects in the slow clearance group had higher exposures (area under the time-concentration curve, AUC) than those in the medium or fast clearance groups. Statistical analyses demonstrated that slower clearance, and/or higher AUC, was correlated with a delay in the need for symptomatic therapy (i.e. dopaminergic therapy) and a reduction in the overall dose of symptomatic therapy, which reached significance in the group with the slowest clearance or highest AUC. In addition, the progression of non-tremor disability in this cohort was slower than that of other groups. Based on the $AUC_{24}$, the average steady-state ($C_{ave,ss}$) plasma concentrations for the fast, medium, and slow clearance groups were 0.9 ng/mL, 1.4 ng/mL, and 2.1 ng/mL, respectively, consistent with the hypothesis that maintaining plasma isradipine concentrations above a threshold (1.5-2 ng/mL) is important for treating PD.

The invention described herein provides methods, uses, and compositions for the treatment of a patient having Parkinson's disease, suspected of having PD, or at risk of having PD; or other neurological conditions, including Lewy Body disease, dementia with Lewy Bodies, supranuclear palsy, multiple system atrophy, or corticobasal degeneration. One aspect of the invention is the treatment of patients having sporadic PD of unknown etiology.

One aspect of the invention is a method comprising administration to a patient in need thereof an oral drug product of dihydropyridine calcium channel blocker, wherein such drug product produces sustained plasma levels of the dihydropyridine calcium channel blocker above a threshold for the majority of the 24-hour day. In one embodiment of the invention, the dihydropyridine calcium channel blocker is isradipine. In another embodiment of the invention, the dihydropyridine calcium channel blocker is chosen from a list consisting of felodipine, nifedipine, amlopidine, nicardipine, nimodipine, and nitrendipine.

In one embodiment of the invention, a composition comprising an oral formulation of isradipine is administered to a patient in need thereof, wherein said formulation provides sustained plasma levels of isradipine above a threshold for the majority of the 24-hour day. In one embodiment of the invention, the oral formulation comprises an extended release excipient that controls the release of isradipine. In one embodiment of the invention, the composition is administered once or twice daily. In one embodiment of the invention, the composition is administered once daily.

BRIEF DESCRIPTION OF THE FIGURES

The accompanying drawings, which are included to provide a further understanding of the present disclosure, are incorporated in and constitute a part of this specification, illustrate aspects of the present disclosure and, together with the detailed description, serve to explain the principles of the present disclosure.

DETAILED DESCRIPTION OF THE INVENTION

The inventors have found that certain therapeutic agents may be administered to patients in need thereof to arrest or slow the progression of neurological diseases such as Parkinson's disease, wherein the efficacy of said therapeutic agents is dependent upon maintaining plasma concentrations above a threshold concentration for the majority of the 24-hour day. As used herein, therapeutic efficacy may be: i) reduced rate of disease progression (relative to the rate of progression during a comparable time period such as 3 months or 6 months for said patient prior to treatment), ii) decreased quantity of dopaminergic therapeutic required for symptom management (relative to similar patients not receiving dihydropyridine calcium channel blocker treatment), iii) delayed onset of need for dopaminergic therapy (relative to similar patients not receiving dihydropyridine calcium channel blocker treatment), iv) improved United Parkinson's Disease Rating Scale (UPDRS) total score (relative to similar patients not receiving dihydropyridine calcium channel blocker treatment), or v) improved UPDRS part III score (relative to similar patients not receiving dihydropyridine calcium channel blocker treatment). In one embodiment, therapeutic efficacy may involve extending the window of utility of dopaminergic therapy, such that dopaminergic therapy can be administered for a longer period of time without inducing debilitating side effects such as motor complications.

The invention described herein includes compositions comprising a dihydropyridine calcium channel blocker to treat a patient with a neurological disease. In one embodiment, the dihydropyridine calcium channel blocker is amlodipine. In one embodiment, the dihydropyridine calcium channel blocker is felodipine. In one embodiment, the dihydropyridine calcium channel blocker is isradipine. In one embodiment, the dihydropyridine calcium channel blocker is nicardipine. In one embodiment, the dihydropyridine calcium channel blocker is nifedipine. In one embodiment, the dihydropyridine calcium channel blocker is nimodipine. In one embodiment, the dihydropyridine calcium channel blocker is nitrendipine. In a preferred embodiment, the dihydropyridine calcium channel blocker is isradipine.

In one embodiment, the dihydropyridine calcium channel blocker is prepared as an oral dosage form. In a preferred embodiment, said oral dosage form is formulated to provide an extended release of the dihydropyridine calcium channel blocker. In a preferred embodiment, the dihydropyridine calcium channel blocker composition is administered orally once or twice daily. In a preferred embodiment, the oral administration of the dihydropyridine calcium channel blocker composition provides a steady state plasma concentration profile for the dihydropyridine calcium channel blocker that is at or above the desired threshold concentration for 12, 14, 15, 16, 17, 18, 19, 20, 21, 22, 23, or 24 hours per day. In a preferred embodiment, administration of said oral dosage form to a patient once or twice per day provides a benefit to said patient selected from the group consisting of reduced rate of disease progression, decreased quantity of dopaminergic therapeutic required for symptom management, delayed onset of need for dopaminergic therapy, improved UPDRS total score, or improved UPDRS part III score. In a preferred embodiment, administration of said oral dosage form to a patient once or twice per day extends the window of utility of dopaminergic therapy.

In one embodiment, the dihydropyridine calcium channel blocker is isradipine and the isradipine is prepared as an oral dosage form. In a preferred embodiment, said oral dosage form is formulated to provide an extended release of the isradipine. In a preferred embodiment, the isradipine composition is administered orally once or twice daily. In a preferred embodiment, the oral administration of the isradipine composition provides a steady state plasma concentration profile for isradipine that is at or above the desired threshold concentration for 12, 14, 15, 16, 17, 18, 19, 20, 21, 22, 23, or 24 hours per day. In a preferred embodiment, administration of said oral dosage form to a patient once or twice per day provides a benefit to said patient selected from the group consisting of reduced rate of disease progression, decreased quantity of dopaminergic therapeutic required for symptom management, delayed onset of need for dopaminergic therapy, improved UPDRS total score, or improved UPDRS part III score. In a preferred embodiment, administration of said oral dosage form to a patient once or twice per day extends the window of utility of dopaminergic therapy.

In one embodiment, the dihydropyridine calcium channel blocker is prepared as a composition for parenteral administration. In a preferred embodiment, said composition is provided with a device for administering said parenteral composition either continuously or at prescribed intervals to provide a steady state plasma concentration profile for the dihydropyridine calcium channel blocker that is at or above the desired threshold concentration for 12, 14, 15, 16, 17, 18, 19, 20, 21, 22, 23, or 24 hours per day. In a preferred embodiment, administration of said parenteral composition to a patient provides a benefit to said patient selected from the group consisting of reduced rate of disease progression, decreased quantity of dopaminergic therapeutic required for symptom management, delayed onset of need for dopaminergic therapy, improved UPDRS total score, or improved UPDRS part III score. In a preferred embodiment, administration of said parenteral composition to a patient extends the window of utility of dopaminergic therapy.

In one embodiment, the dihydropyridine calcium channel blocker is isradipine and is prepared as a composition for parenteral administration. In a preferred embodiment, said composition is provided with a device for administering said parenteral composition either continuously or at prescribed intervals to provide a steady state plasma concentration profile for isradipine that is at or above the desired threshold concentration for 12, 14, 15, 16, 17, 18, 19, 20, 21, 22, 23, or 24 hours per day. In a preferred embodiment, administration of said parenteral isradipine composition to a patient provides a benefit to said patient selected from the group consisting of reduced rate of disease progression, decreased quantity of dopaminergic therapeutic required for symptom management, delayed onset of need for dopaminergic therapy, improved UPDRS total score, or improved UPDRS part III score. In a preferred embodiment, administration of said parenteral isradipine composition to a patient extends the window of utility of dopaminergic therapy.

One aspect of the invention is a method of administering to a patient in need thereof, a composition comprising isradipine over a period of 4 weeks, 8 weeks, 3 months, 6 months, 9 months, 12 months, 18 months, 24 months, 36 months, or longer. In one aspect of repeated administration of a composition comprising isradipine to a patient with Parkinson's disease, the UPDRS total scores for said patient over a period of 3 months, 6 months, 9 months, 12 months indicate a slower rate of decline relative to a patient with Parkinson's disease not receiving said isradipine composition. In one aspect of repeated administration of a composition comprising isradipine to a patient with Parkinson's disease, the UPDRS part III scores for said patient over a period of 3 months, 6 months, 9 months, 12 months indicate a slower rate of decline relative to a patient with Parkinson's disease not receiving said isradipine composition. In one aspect of repeated administration of a composition comprising isradipine to a patient with Parkinson's disease over a period of 3 months, 6 months, 9 months, 12 months 18 months, 24 months, 36 months, the lack of accumulated impairment indicate a reduced need for dopaminergic therapy relative to a patient with Parkinson's disease not receiving said isradipine composition. In this aspect, a reduced need for dopaminergic therapy may be determined by a lower dose of dopaminergic therapy relative to that required for a patient not receiving said isradipine composition; alternatively the reduced need for dopaminergic therapy may be determined by a delayed onset for the need in dopaminergic therapy relative to that required for a patient not receiving said isradipine composition. In one aspect of repeated administration of a composition comprising isradipine to a patient with Parkinson's disease over a period of 6 months, 9 months, 12 months 18 months, 24 months, 36 months, 48 months, or longer, the lack of, or reduced incidence of, motor complications indicates an extension in the window of utility of dopaminergic therapy relative to that of a patient not receiving said isradipine composition.

In one embodiment of the invention, the dihydropyridine calcium channel blocker is isradipine and the daily dose of isradipine is 3 mg to 15 mg. In a preferred embodiment of the invention, the daily dose of isradipine is 5 mg to 15 mg. In a preferred embodiment of the invention, the daily dose of isradipine is 6 mg to 15 mg. In a preferred embodiment of the invention, the daily dose of isradipine is 7 mg to 15 mg. In a preferred embodiment of the invention, the daily dose of isradipine is 8 mg to 15 mg. In a preferred embodiment of the invention, the daily dose of isradipine is 9 mg to 15 mg. In a preferred embodiment of the invention, the daily dose of isradipine is 10 mg to 15 mg. In a preferred embodiment of the invention, the daily dose of isradipine is 5 mg to 12 mg. In a preferred embodiment of the invention, the daily dose of isradipine is 6 mg to 12 mg. In a preferred embodiment of the invention, the daily dose of isradipine is 7 mg to 12 mg. In a preferred embodiment of the invention, the daily dose of isradipine is 8 mg to 12 mg. In a preferred embodiment of the invention, the daily dose of isradipine is 9 mg to 12 mg. In a preferred embodiment of the invention, the daily dose of isradipine is 10 mg to 12 mg. In a preferred embodiment of the invention, the daily dose of isradipine is 7 mg to 15 mg. In a preferred embodiment of the invention, the daily dose of isradipine is 8 mg to 15 mg. In a preferred embodiment of the invention, the daily dose of isradipine is 9 mg to 15 mg. In a preferred embodiment of the invention, the daily dose of isradipine is 10 mg.

In one embodiment of the invention, the desired threshold plasma concentration for the dihydropyridine calcium channel blocker at steady state is 1.0 ng/ml. In one embodiment of the invention, the desired threshold plasma concentration for the dihydropyridine calcium channel blocker at steady state is 1.2 ng/ml. In one embodiment of the invention, the desired threshold plasma concentration for the dihydropyridine calcium channel blocker at steady state is 1.3 ng/ml. In one embodiment of the invention, the desired threshold plasma concentration for the dihydropyridine calcium channel blocker at steady state is 1.4 ng/ml. In one embodiment of the invention, the desired threshold plasma concentration for the dihydropyridine calcium channel blocker at steady state is 1.5 ng/ml. In one embodiment of the invention, the desired threshold plasma concentration for the dihydropyridine calcium channel blocker at steady state is 1.6 ng/ml. In one embodiment of the invention, the desired threshold plasma concentration for the dihydropyridine calcium channel blocker at steady state is 1.7 ng/ml. In one embodiment of the invention, the desired threshold plasma concentration for the dihydropyridine calcium channel blocker at steady state is 1.75 ng/ml. In one embodiment of the invention, the desired threshold plasma concentration for the dihydropyridine calcium channel blocker at steady state is 1.8 ng/ml. In one embodiment of the invention, the desired threshold plasma concentration for the dihydropyridine calcium channel blocker at steady state is 1.9 ng/ml. In one embodiment of the invention, the desired threshold plasma concentration for the dihydropyridine calcium channel blocker at steady state is 2.0 ng/ml. In one embodiment of the invention, the desired threshold plasma concentration for the dihydropyridine calcium channel blocker at steady state is 2.1 ng/ml. In one embodiment of the invention, the desired threshold plasma concentration for the dihydropyridine calcium channel blocker at steady state is 2.2 ng/ml. In one embodiment of the invention, the desired threshold plasma concentration for the dihydropyridine calcium channel blocker at steady state is 2.3 ng/ml. In one embodiment of the invention, the desired threshold plasma concentration for the dihydropyridine calcium channel blocker at steady state is 2.4 ng/ml. In one embodiment of the invention, the desired threshold plasma concentration for the dihydropyridine calcium channel blocker at steady state is 2.5 ng/ml. In one embodiment of the invention, the desired threshold plasma concentration for the dihydropyridine calcium channel blocker at steady state is 2.6 ng/ml. In one embodiment of the invention, the dihydropyridine calcium channel blocker is isradipine and the threshold plasma concentration for isradipine at steady state is 1.0 ng/ml. In one embodiment of the invention, the dihydropyridine calcium channel blocker is isradipine and the threshold plasma concentration for isradipine at steady state is 1.2 ng/ml. In one embodiment of the invention, the dihydropyridine calcium channel blocker is isradipine and the threshold plasma concentration for isradipine at steady state is 1.3 ng/ml. In one embodiment of the invention, the dihydropyridine calcium channel blocker is isradipine and the threshold plasma concentration for isradipine at steady state is 1.4 ng/ml. In one embodiment of the invention, the dihydropyridine calcium channel blocker is isradipine and the threshold plasma concentration for isradipine at steady state is 1.5 ng/ml. In one embodiment of the invention, the dihydropyridine calcium channel blocker is isradipine and the threshold plasma concentration for isradipine at steady state is 1.6 ng/ml. In one embodiment of the invention, the dihydropyridine calcium channel blocker is isradipine and the threshold plasma concentration for isradipine at steady state is 1.7 ng/ml. In one embodiment of the invention, the dihydropyridine calcium channel blocker is isradipine and the threshold plasma concentration for isradipine at steady state is 1.75 ng/ml. In one embodiment of the invention, the dihydropyridine calcium channel blocker is isradipine and the threshold plasma concentration for isradipine at steady state is 1.8 ng/ml. In one embodiment of the invention, the dihydropyridine calcium channel blocker is isradipine and the threshold plasma concentration for isradipine at steady state is 1.9 ng/ml. In one embodiment of the invention, the dihydropyridine calcium channel blocker is isradipine and the threshold plasma concentration for isradipine at steady state is 2.0 ng/ml. In one embodiment of the invention, the dihydropyridine calcium channel blocker is isradipine and the threshold plasma concentration for isradipine at steady state is 2.1 ng/ml. In one embodiment of the invention, the dihydropyridine calcium channel blocker is isradipine and the threshold plasma concentration for isradipine at steady state is 2.2 ng/ml. In one embodiment of the invention, the dihydropyridine calcium channel blocker is isradipine and the threshold plasma concentration for isradipine at steady state is 2.3 ng/ml. In one embodiment of the invention, the dihydropyridine calcium channel blocker is isradipine and the threshold plasma concentration for isradipine at steady state is 2.4 ng/ml. In one embodiment of the invention, the dihydropyridine calcium channel blocker is isradipine and the threshold plasma concentration for isradipine at steady state is 2.5 ng/ml. In one embodiment of the invention, the dihydropyridine calcium channel blocker is isradipine and the threshold plasma concentration for isradipine at steady state is 2.6 ng/ml.

In one embodiment of the invention, the repeated administration of the composition to a patient provides a steady state plasma profile characterized by a dihydropyridine calcium channel blocker concentration throughout the dosing interval (Css) of 1.5 to 3.5 ng/ml for at least 12 hours per 24 hour period. In one embodiment of the invention, the repeated administration of the composition to a patient provides a steady state plasma profile characterized by a dihydropyridine calcium channel blocker concentration throughout the dosing interval (Css) of 1.5 to 3.5 ng/ml for at least 14 hours per 24 hour period. In one embodiment of the invention, the repeated administration of the composition to a patient provides a steady state plasma profile characterized by a dihydropyridine calcium channel blocker concentration throughout the dosing interval (Css) of 1.5 to 3.5 ng/ml for at least 15 hours per 24 hour period. In one embodiment of the invention, the repeated administration of the composition to a patient provides a steady state plasma profile characterized by a dihydropyridine calcium channel blocker concentration throughout the dosing interval (Css) of 1.5 to 3.5 ng/ml for at least 16 hours per 24 hour period. In one embodiment of the invention, the repeated administration of the composition to a patient provides a steady state plasma profile characterized by a dihydropyridine calcium channel blocker concentration throughout the dosing interval (Css) of 1.5 to 3.5 ng/ml for at least 17 hours per 24 hour period. In one embodiment of the invention, the repeated administration of the composition to a patient provides a steady state plasma profile characterized by a dihydropyridine calcium channel blocker concentration throughout the dosing interval (Css) of 1.5 to 3.5 ng/ml for at least 18 hours per 24 hour period. In one embodiment of the invention, the repeated administration of the composition to a patient provides a steady state plasma profile characterized by a dihydropyridine calcium channel blocker concentration throughout the dosing interval (Css) of 1.5 to 3.5 ng/ml for at least 19 hours per 24 hour period. In one embodiment of the invention, the repeated administration of the composition to a patient provides a steady state plasma profile characterized by a dihydropyridine calcium channel blocker concentration throughout the dosing interval (Css) of 1.5 to 3.5 ng/ml for at least 20 hours per 24 hour period. In one embodiment of the invention, the repeated administration of the composition to a patient provides a steady state plasma profile characterized by a dihydropyridine calcium channel blocker concentration throughout the dosing interval (Css) of 1.5 to 3.5 ng/ml for at least 21 hours per 24 hour period. In one embodiment of the invention, the repeated administration of the composition to a patient provides a steady state plasma profile characterized by a dihydropyridine calcium channel blocker concentration throughout the dosing interval (Css) of 1.5 to 3.5 ng/ml for at least 22 hours per 24 hour period. In one embodiment of the invention, the repeated administration of the composition to a patient provides a steady state plasma profile characterized by a dihydropyridine calcium channel blocker concentration throughout the dosing interval (Css) of 1.5 to 3.5 ng/ml for at least 23 hours per 24 hour period.

In one embodiment of the invention, the dihydropyridine calcium channel blocker is isradipine and repeated administration of the composition to a patient provides a steady state plasma profile characterized by an isradipine concentration throughout the dosing interval (Css) of 1.5 to 3.5 ng/ml for at least 12 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.5 to 3.5 ng/ml for at least 14 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.5 to 3.5 ng/ml for at least 15 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.5 to 3.5 ng/ml for at least 16 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.5 to 3.5 ng/ml for at least 17 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.5 to 3.5 ng/ml for at least 18 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.5 to 3.5 ng/ml for at least 19 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.5 to 3.5 ng/ml for at least 20 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.5 to 3.5 ng/ml for at least 21 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.5 to 3.5 ng/ml for at least 22 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.5 to 3.5 ng/ml for at least 23 hours per 24 hour period.

In one embodiment of the invention, the repeated administration of the composition to a patient provides a steady state plasma profile characterized by a dihydropyridine calcium channel blocker concentration throughout the dosing interval (Css) of 1.75 to 3.5 ng/ml for at least 12 hours per 24 hour period. In one embodiment of the invention, the repeated administration of the composition to a patient provides a steady state plasma profile characterized by a dihydropyridine calcium channel blocker concentration throughout the dosing interval (Css) of 1.75 to 3.5 ng/ml for at least 14 hours per 24 hour period. In one embodiment of the invention, the repeated administration of the composition to a patient provides a steady state plasma profile characterized by a dihydropyridine calcium channel blocker concentration throughout the dosing interval (Css) of 1.75 to 3.5 ng/ml for at least 15 hours per 24 hour period. In one embodiment of the invention, the repeated administration of the composition to a patient provides a steady state plasma profile characterized by a dihydropyridine calcium channel blocker concentration throughout the dosing interval (Css) of 1.75 to 3.5 ng/ml for at least 16 hours per 24 hour period. In one embodiment of the invention, the repeated administration of the composition to a patient provides a steady state plasma profile characterized by a dihydropyridine calcium channel blocker concentration throughout the dosing interval (Css) of 1.75 to 3.5 ng/ml for at least 17 hours per 24 hour period. In one embodiment of the invention, the repeated administration of the composition to a patient provides a steady state plasma profile characterized by a dihydropyridine calcium channel blocker concentration throughout the dosing interval (Css) of 1.75 to 3.5 ng/ml for at least 18 hours per 24 hour period. In one embodiment of the invention, the repeated administration of the composition to a patient provides a steady state plasma profile characterized by a dihydropyridine calcium channel blocker concentration throughout the dosing interval (Css) of 1.75 to 3.5 ng/ml for at least 19 hours per 24 hour period. In one embodiment of the invention, the repeated administration of the composition to a patient provides a steady state plasma profile characterized by a dihydropyridine calcium channel blocker concentration throughout the dosing interval (Css) of 1.75 to 3.5 ng/ml for at least 20 hours per 24 hour period. In one embodiment of the invention, the repeated administration of the composition to a patient provides a steady state plasma profile characterized by a dihydropyridine calcium channel blocker concentration throughout the dosing interval (Css) of 1.75 to 3.5 ng/ml for at least 21 hours per 24 hour period. In one embodiment of the invention, the repeated administration of the composition to a patient provides a steady state plasma profile characterized by a dihydropyridine calcium channel blocker concentration throughout the dosing interval (Css) of 1.75 to 3.5 ng/ml for at least 22 hours per 24 hour period. In one embodiment of the invention, the repeated administration of the composition to a patient provides a steady state plasma profile characterized by a dihydropyridine calcium channel blocker concentration throughout the dosing interval (Css) of 1.75 to 3.5 ng/ml for at least 23 hours per 24 hour period.

In one embodiment of the invention, the dihydropyridine calcium channel blocker is isradipine and repeated administration of the composition to a patient provides a steady state plasma profile characterized by an isradipine concentration throughout the dosing interval (Css) of 1.75 to 3.5 ng/ml for at least 12 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.75 to 3.5 ng/ml for at least 14 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.75 to 3.5 ng/ml for at least 15 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.75 to 3.5 ng/ml for at least 16 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.75 to 3.5 ng/ml for at least 17 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.75 to 3.5 ng/ml for at least 18 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.75 to 3.5 ng/ml for at least 19 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.75 to 3.5 ng/ml for at least 20 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.75 to 3.5 ng/ml for at least 21 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.75 to 3.5 ng/ml for at least 22 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 1.75 to 3.5 ng/ml for at least 23 hours per 24 hour period.

In one embodiment of the invention, the repeated administration of the composition to a patient provides a steady state plasma profile characterized by a dihydropyridine calcium channel blocker concentration throughout the dosing interval (Css) of 2.0 to 3.5 ng/ml for at least 12 hours per 24 hour period. In one embodiment of the invention, the repeated administration of the composition to a patient provides a steady state plasma profile characterized by a dihydropyridine calcium channel blocker concentration throughout the dosing interval (Css) of 2.0 to 3.5 ng/ml for at least 14 hours per 24 hour period. In one embodiment of the invention, the repeated administration of the composition to a patient provides a steady state plasma profile characterized by a dihydropyridine calcium channel blocker concentration throughout the dosing interval (Css) of 2.0 to 3.5 ng/ml for at least 15 hours per 24 hour period. In one embodiment of the invention, the repeated administration of the composition to a patient provides a steady state plasma profile characterized by a dihydropyridine calcium channel blocker concentration throughout the dosing interval (Css) of 2.0 to 3.5 ng/ml for at least 16 hours per 24 hour period. In one embodiment of the invention, the repeated administration of the composition to a patient provides a steady state plasma profile characterized by a dihydropyridine calcium channel blocker concentration throughout the dosing interval (Css) of 2.0 to 3.5 ng/ml for at least 17 hours per 24 hour period. In one embodiment of the invention, the repeated administration of the composition to a patient provides a steady state plasma profile characterized by a dihydropyridine calcium channel blocker concentration throughout the dosing interval (Css) of 2.0 to 3.5 ng/ml for at least 18 hours per 24 hour period. In one embodiment of the invention, the repeated administration of the composition to a patient provides a steady state plasma profile characterized by a dihydropyridine calcium channel blocker concentration throughout the dosing interval (Css) of 2.0 to 3.5 ng/ml for at least 19 hours per 24 hour period. In one embodiment of the invention, the repeated administration of the composition to a patient provides a steady state plasma profile characterized by a dihydropyridine calcium channel blocker concentration throughout the dosing interval (Css) of 2.0 to 3.5 ng/ml for at least 20 hours per 24 hour period. In one embodiment of the invention, the repeated administration of the composition to a patient provides a steady state plasma profile characterized by a dihydropyridine calcium channel blocker concentration throughout the dosing interval (Css) of 2.0 to 3.5 ng/ml for at least 21 hours per 24 hour period. In one embodiment of the invention, the repeated administration of the composition to a patient provides a steady state plasma profile characterized by a dihydropyridine calcium channel blocker concentration throughout the dosing interval (Css) of 2.0 to 3.5 ng/ml for at least 22 hours per 24 hour period. In one embodiment of the invention, the repeated administration of the composition to a patient provides a steady state plasma profile characterized by a dihydropyridine calcium channel blocker concentration throughout the dosing interval (Css) of 2.0 to 3.5 ng/ml for at least 23 hours per 24 hour period.

In one embodiment of the invention, the dihydropyridine calcium channel blocker is isradipine and repeated administration of the composition to a patient provides a steady state plasma profile characterized by an isradipine concentration throughout the dosing interval (Css) of 2.0 to 3.5 ng/ml for at least 12 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 2.0 to 3.5 ng/ml for at least 14 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 2.0 to 3.5 ng/ml for at least 15 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 2.0 to 3.5 ng/ml for at least 16 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 2.0 to 3.5 ng/ml for at least 17 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 2.0 to 3.5 ng/ml for at least 18 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 2.0 to 3.5 ng/ml for at least 19 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 2.0 to 3.5 ng/ml for at least 20 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 2.0 to 3.5 ng/ml for at least 21 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 2.0 to 3.5 ng/ml for at least 22 hours per 24 hour period. In one embodiment of the invention, the dihydropyridine calcium channel blocker is isradipine and repeated administration of the composition to a patient provides a steady state plasma profile characterized by an isradipine concentration throughout the dosing interval (Css) of 2.0 to 3.5 ng/ml for at least 23 hours per 24 hour period.

In one embodiment of the invention, the repeated administration of the composition to a patient provides a steady state plasma profile with a fluctuation that is less than the fluctuation determined for an immediate release form of the dihydropyridine calcium channel blocker in an immediate release form administered once or twice per day. As used herein, fluctuation is defined as the $(C_{max,ss} - C_{min,ss})/C_{ave,ss} \times 100\%$, where $C_{max,ss}$ is the maximum concentration for the dihydropyridine calcium channel blocker at steady state, $C_{min,ss}$ is the minimum concentration for the dihydropyridine calcium channel blocker at steady state, and $C_{ave,ss}$ is the mean concentration for the dihydropyridine calcium channel blocker at steady state. In one embodiment, the fluctuation observed at steady state for the dihydropyridine calcium channel blocker is less than 130%. In one embodiment, the fluctuation observed at steady state for the dihydropyridine calcium channel blocker is less than 120%. In one embodiment, the fluctuation observed at steady state for the dihydropyridine calcium channel blocker is less than 110%. In one embodiment, the fluctuation observed at steady state for the dihydropyridine calcium channel blocker is less than 100%. In one embodiment, the fluctuation observed at steady state for the dihydropyridine calcium channel blocker is less than 90%. In one embodiment, the fluctuation observed at steady state for the dihydropyridine calcium channel blocker is less than 80%. In one embodiment, the fluctuation observed at steady state for the dihydropyridine calcium channel blocker is less than 70%. In one embodiment, the fluctuation observed at steady state for the dihydropyridine calcium channel blocker is less than 60%. In one embodiment, the fluctuation observed at steady state for the dihydropyridine calcium channel blocker is less than 50%. In one embodiment, the fluctuation observed at steady state for the dihydropyridine calcium channel blocker is less than 40%. In one embodiment, the dihydropyridine calcium channel blocker is isradipine and the fluctuation observed at steady state for isradipine is less than 130%. In one embodiment, the dihydropyridine calcium channel blocker is isradipine and the fluctuation observed at steady state for isradipine is less than 120%. In one embodiment, the dihydropyridine calcium channel blocker is isradipine and the fluctuation observed at steady state for isradipine is less than 110%. In one embodiment, the dihydropyridine calcium channel blocker is isradipine and the fluctuation observed at steady state for isradipine is less than 100%. In one embodiment, the dihydropyridine calcium channel blocker is isradipine and the fluctuation observed at steady state for isradipine is less than 90%. In one embodiment, the dihydropyridine calcium channel blocker is isradipine and the fluctuation observed at steady state for isradipine is less than 80%. In one embodiment, the dihydropyridine calcium channel blocker is isradipine and the fluctuation observed at steady state for isradipine is less than 70%. In one embodiment, the dihydropyridine calcium channel blocker is isradipine and the fluctuation observed at steady state for isradipine is less than 60%. In one embodiment, the dihydropyridine calcium channel blocker is isradipine and the fluctuation observed at steady state for isradipine is less than 50%. In one embodiment, the dihydropyridine calcium channel blocker is isradipine and the fluctuation observed at steady state for isradipine is less than 40%.

In one embodiment of the invention, the repeated administration of the composition to a patient provides a steady state plasma profile for the dihydropyridine calcium channel blocker characterized by a $C_{max,ss}$ that is less than 0.5 ng/ml multiplied by the total daily dose of the dihydropyridine calcium channel blocker in milligrams. For example, a total daily dose of isradipine at 10 mg would provide a $C_{max,ss}$ that is less than 5 ng/ml. In one embodiment of the invention, the repeated administration of the composition to a patient provides a steady state plasma profile for the dihydropyridine calcium channel blocker characterized by a $C_{max,ss}$ that is less than 0.45 ng/ml multiplied by the total daily dose of the dihydropyridine calcium channel blocker in milligrams. In one embodiment of the invention, the repeated administration of the composition to a patient provides a steady state plasma profile for the dihydropyridine calcium channel blocker characterized by a $C_{max,ss}$ that is less than 0.4 ng/ml multiplied by the total daily dose of the dihydropyridine calcium channel blocker in milligrams. In one embodiment of the invention, the repeated administration of the composition to a patient provides a steady state plasma profile for the dihydropyridine calcium channel blocker characterized by a $C_{max,ss}$ that is less than 0.35 ng/ml multiplied by the total daily dose of the dihydropyridine calcium channel blocker in milligrams. In one embodiment of the invention, the repeated administration of the composition to a patient provides a steady state plasma profile for the dihydropyridine calcium channel blocker characterized by a $C_{max,ss}$ that is less than 0.3 ng/ml multiplied by the total daily dose of the dihydropyridine calcium channel blocker in milligrams. In one embodiment, an oral composition comprising isradipine administered to a patient in need thereof twice per day at a total daily dose of 10 mg provides a steady state profile for isradipine characterized by a $C_{max,ss}$ of less than 4.5 ng/ml, 4.0 ng/ml, 3.5 ng/ml, 3.0 ng/ml. In one embodiment, an oral composition comprising isradipine administered to a patient in need thereof once daily at a dose of 10 mg provides a steady state profile for isradipine characterized by a $C_{max,ss}$ of less than 4.5 ng/ml, 4.0 ng/ml, 3.5 ng/ml, 3.0 ng/ml.

In one embodiment of the invention, the repeated administration of the composition to a patient provides a steady state plasma profile for the dihydropyridine calcium channel blocker characterized by a $C_{min,ss}$ that is 0.1 to 0.3 ng/ml multiplied by the total daily dose of the dihydropyridine calcium channel blocker in milligrams. For example, a total daily dose of isradipine at 10 mg would provide a $C_{min,ss}$ that is 1.0 to 3.0 ng/ml. In one embodiment of the invention, the repeated administration of the composition to a patient provides a steady state plasma profile for the dihydropyridine calcium channel blocker characterized by a $C_{min,ss}$ that is 0.12 to 0.3 ng/ml multiplied by the total daily dose of the dihydropyridine calcium channel blocker in milligrams. In one embodiment of the invention, the repeated administration of the composition to a patient provides a steady state plasma profile for the dihydropyridine calcium channel blocker characterized by a $C_{min,ss}$ that is 0.14 to 0.3 ng/ml multiplied by the total daily dose of the dihydropyridine calcium channel blocker in milligrams. In one embodiment of the invention, the repeated administration of the composition to a patient provides a steady state plasma profile for the dihydropyridine calcium channel blocker characterized by a $C_{min,ss}$ that is 0.16 to 0.3 ng/ml multiplied by the total daily dose of the dihydropyridine calcium channel blocker in milligrams. In one embodiment of the invention, the repeated administration of the composition to a patient provides a steady state plasma profile for the dihydropyridine calcium channel blocker characterized by a $C_{min,ss}$ that is 0.18 to 0.3 ng/ml multiplied by the total daily dose of the dihydropyridine calcium channel blocker in milligrams. In one embodiment of the invention, the repeated administration of the composition to a patient provides a steady state plasma profile for the dihydropyridine calcium channel blocker characterized by a $C_{min,ss}$ that is 0.20 to 0.3 ng/ml multiplied by the total daily dose of the dihydropyridine calcium channel blocker in milligrams. In one embodiment, an oral composition comprising isradipine administered to a patient in need thereof twice per day at a total daily dose of 10 mg provides a steady state profile for isradipine characterized by a $C_{min,ss}$ of 1.0 to 3.0 ng/ml, 1.2 to 3.0 ng/ml, 1.4 to 3.0 ng/ml, 1.6 to 3.0 ng/ml, 1.8 to 3.0 ng/ml, 2.0 to 3.0 ng/ml. In one embodiment, an oral composition comprising isradipine administered to a patient in need thereof once daily at a dose of 10 mg provides a steady state profile for isradipine characterized by a $C_{min,ss}$ of 1.0 to 3.0 ng/ml, 1.2 to 3.0 ng/ml, 1.4 to 3.0 ng/ml, 1.6 to 3.0 ng/ml, 1.8 to 3.0 ng/ml, 2.0 to 3.0 ng/ml.

EXAMPLES

Example 1. Post-Hoc Analysis of STEADY-PD II

The dataset used in this study is from the Safety, Tolerability and Efficacy Assessment of Dynacirc CR in Parkinson Disease (Steady-PD II) multicenter clinical trial. The study population, study design and procedures have been described previously (Parkinson Study, 2013). In brief, this was a Phase 2, randomized, double-blind parallel group trial to establish a dosage of isradipine controlled-release (CR) that is tolerable and demonstrates preliminary efficacy for a future larger efficacy trial. Participants included men and women age 30 years and above with a diagnosis of early PD made within 3 years of randomization with Hoehn and Yahr stage<=2.5 who did not require dopaminergic therapy. Participants were randomized to 5, 10, or 20 mg of isradipine CR or matching placebo administered once daily and followed for 12 months (52 weeks). UPDRS and other clinical assessments were performed at baseline, weeks 2, 4, 6, 8, 12, and every 3 months thereafter.

For the post-hoc analysis of efficacy, descriptive statistics were computed including the number and percent of participants who were ever on rasagiline, who started symptomatic medication during the study period, and who completed the week 52 visit stratified by treatment group. Differences in mean baseline UPDRS score by treatment group was assessed using analysis of variance (ANOVA) test.

The primary analysis used analysis of covariance (ANCOVA) to examine the change in the UPDRS score from baseline to 52 weeks as the outcome, with assigned treatment group as the primary predictor of interest, and baseline UPDRS score included as a covariate (Ciolino et al., 2015; Egbewale, Lewis, & Sim, 2014). ANCOVA assumptions were checked and confirmed: independence of treatment group and baseline UPDRS was checked by the ANOVA of baseline UPDRS by treatment group; homogeneity of slopes was checked by evaluating addition of an interaction term for treatment*baseline; and normality assumptions were checked by examining residual by predicted distributions and Q-Q plots of residuals.

Due to tolerability issues, some participants assigned to the 20 mg isradipine group were titrated to 15 mg isradipine. The proportion with 52 week follow up was significantly lower in these groups (75% in 15 mg group, 80% in 20 mg group, 96% in other groups). Therefore, the 20 mg group was excluded from analyses.

The change in the total UPDRS scores (parts I, II, and III, which assess both motor and non-motor impairments) from baseline to 52 weeks for placebo, 5 mg, and 10 mg/day ER isradipine groups were 4.12, 2.64, and 0.24, respectively, with the higher value indicating greater impairment. The ANCOVA analysis demonstrated that the change in total UPDRS scores were significantly different between the 10 mg group and the placebo group (p=0.04), demonstrating that 10 mg ER isradipine significantly reduced PD impairment as determined by total UPDRS scores.

In addition, the change from baseline to 52 weeks in part III UPDRS scores (which assesses motor impairments, which are the cardinal symptoms of PD) for the placebo, 5 mg, and 10 mg/day ER isradipine were 1.96, 1.00, and −0.80, respectively. Similarly, the ANCOVA analysis demonstrated that the change in the part III UPDRS scores were significantly different between the 10 mg group and the placebo group (p=0.036), demonstrating that 10 mg ER isradipine significantly reduced motor impairment as determined by the part III UPDRS scores.

These results indicate that treatment with 10 mg a day of an extended release (ER) formulation of isradipine significantly reduces PD impairment (both motor and non-motor) compared to placebo.

Example 2. Simulations of the Steady-State PK Profile of ER and IR Isradipine

In order to understand how the same daily dose of isradipine (10 mg) resulted in vastly different outcomes when administered as an ER form (STEADY-PD II) compared to an IR form (STEADY-PD III), we simulated the steady-state pharmacokinetic profiles for ER and IR isradipine following the same regimens used in the STEADY-PD trials (10 mg ER isradipine QD in STEADY-PD II and 5 mg IR isradipine BID in STEADY-PD III). Using the single dose PK parameters for ER and IR isradipine published by Carrara et al. 1994 (which utilized a different ER formulation than the formulation used in STEADY-PD II), the predicted steady-state plasma concentration-time profiles for the ER and IR formulations were generated by using the non-parametric superposition tool in WinNonlin. The predicted steady-state PK profile of 10 mg QD ER isradipine showed a relatively flat profile with minimal peak-to-trough fluctuations, compared to the predicted profile for 5 mg BID IR isradipine, which showed pronounced peaks and troughs and larger peak-to-trough fluctuations (FIG. 1, Table 1). The predicted Cmax for 5 mg BID IR isradipine was approximately 1.7-fold higher, and the predicted Cmin was 3.7-fold lower, than for 10 mg QD ER isradipine. The 24-hour Cave for the 10 mg QD ER isradipine was approximately 1.8 ng/mL, higher than the Cave of 1.4 ng/mL for 5 mg BID IR isradipine. Importantly, the time in which plasma concentrations were above the threshold of 1.5 ng/mL was 21 hours for 10 mg QD ER isradipine, compared to 8 hours for 5 mg BID IR isradipine. Based on these results, it is concluded that higher Cmin, higher Cave, and more time above threshold are important parameters for the efficacy of isradipine for the treatment of PD. In addition, as a high Cmax is often associated with side effects, an isradipine preparation that maintains these parameters (Cmin, Cave, time above threshold) while minimizing Cmax would provide the most suitable therapeutic option for the treatment of PD. Thus, as shown in Table 1, the 10 mg QD ER isradipine regimen has a much lower fluctuation (as defined by Cmax−Cmin/Cave) compared to the 5 mg BID IR regimen, and is expected to have greater therapeutic potential.

TABLE 1

Isradipine pharmacokinetic parameters based on predictions of steady-state profiles

| Steady-State Parameter | 10 mg QD ER | 5 mg BID IR |
| --- | --- | --- |
| $C_{max,ss}$ (ng/mL) | 2.7 | 4.6 |
| $C_{min,ss}$ (ng/mL) | 1.4 | 0.4 |
| $C_{ave,ss}$ (ng/mL) | 1.8 | 1.4 |
| Time above threshold (1.5 ng/mL) (hour) | 21 | 8 |
| Fluctuation (%) | 66 | 307 |

Example 3. Post-Hoc Analyses of STEADY-PD III

In order to further examine the pharmacokinetic-pharmacodynamic relationship of isradipine in PD, we conducted a post-hoc analysis of the STEADY-PD III trial. STEADY-PD III was a phase 3, multi-center, randomized, double-blind, placebo-controlled trial (NCT02168842) to determine the effects of isradipine on slowing the clinical progression of PD(9). Study participants were randomized 1:1 to receive either IR-isradipine 5-mg twice daily or placebo for a treatment duration of 36 months.

Plasma samples for measurement of isradipine concentrations were collected from all randomized study participants. Samples were collected at screening to ensure absence of isradipine administration outside of the trial, and at study months 3 and 6 following baseline visit. On the day of the 3-month visit, participants withheld their morning dose of study drug in order to collect a post-dose sample approximately 12 hours since last dose. At the same visit, a second plasma sample was collected approximately 2-3 hours following an in-clinic dose of study drug. For the 6-month study visit, a plasma sample was collected 4-8 hours after study drug intake.

Population pharmacokinetic modeling of plasma isradipine concentrations were performed using nonlinear mixed-effects modeling (NONMEM v7.4.0; ICON Development Solutions, Ellicott City, MD). One- and two-compartment models with linear absorption and elimination were evaluated with up to three transit compartments and a lag-time for describing drug absorption. Interindividual variability was assumed log-normally distributed. Additive, proportional, and mixed residual variability functions were tested for quantifying unexplained variability. The pharmacokinetic model was used to estimate individual Bayesian estimates of apparent oral clearance (CL/F) for an individual. CL/F is the measure of the ability of the body to eliminate drug via metabolism and elimination following an oral dose with a bioavailability of F. CL/F is inversely related to the area under the concentration-time curve (AUC).

Time to need antiparkinson medication in relation to isradipine exposure was assessed using Cox proportional hazards models. Values of CL/F and $AUC_{24}$ were evaluated as evenly divided tertile groups: fast, middle, and slow for CL/F; and, low, middle, and high for $AUC_{24}$. The tertile groups were evaluated as a continuous parameter and as a nominal variable. The placebo arm participants (n=166) were defined as the reference group.

Among the 166 participants with an estimated isradipine CL/F, there were up to 162 participants with clinical outcomes data at baseline and month 36. The isradipine pharmacokinetic parameters for each tertile group are shown in Table 2. With decreasing clearance (CL/F) or increasing exposure (AUC), there was a trend towards higher Cmin and Cave, with subjects in the slow CL/F and high AUC tertile having the highest Cmin and Cave compared to the other tertiles. In addition, the mean PK profiles for subjects in each tertile was simulated based on the population PK model. Importantly, the simulated profiles demonstrated that there was a trend toward increasing time above therapeutic threshold (1.5 ng/mL) with slower clearance and higher exposure. Specifically, the time above threshold for the low, middle, and higher exposure groups were 2, 10, and 23 hours, respectively.

TABLE 2

Steady-state isradipine pharmacokinetic parameters by tertile groups

| Steady-State Parameter | Isradipine Exposure Group | | |
| --- | --- | --- | --- |
| | Fast CL/F, Low $AUC_{24}$ | Middle CL/F, Middle $AUC_{24}$ | Slow CL/F, High $AUC_{24}$ |
| CL/F (liters/hour) | 477 | 296 | 195 |
| $AUC_{24}$ (ng * h/mL) | 21.6 | 32.9 | 49.8 |
| $C_{ave,ss}$ (ng/mL) | 0.9 | 1.4 | 2.1 |
| $C_{max,ss}$ (ng/mL) | 1.86 | 3.28 | 4.90 |
| $C_{min,ss}$ (ng/mL) | 0.56 | 0.86 | 1.40 |
| Time above threshold (1.5 ng/mL) (hour) | 2 | 10 | 23 |

Time to first initiation of antiparkinson therapy was evaluated in relation to isradipine exposure, with the placebo group (n=166) defined as the reference group. Compared to the placebo group, when testing for a trend for each CL/F tertile decrement from fast to middle to slow, or $AUC_{24}$ increment from low to middle to high, the risk of needing antiparkinson treatment was decreased by 13% (HR:0.87, 95% CI:0.78-0.98, p-value for trend=0.02). When evaluating tertile groups as a nominal variable, the association between isradipine CL/F and time to need antiparkinson therapy did not reach statistical significance in CL/F tertile groups. However, when considering $AUC_{24}$, which accounts for the dose of isradipine administered, the highest exposure isradipine group was associated with a reduced HR for time to need therapy compared to the placebo group (HR:0.66, 95% CI0.45-0.97). These results were similar when adjusting the Cox proportional hazard models for sex or age.

There was a modest statistically significant correlation between cumulative levodopa equivalent dose (milligram-years) required through the 36-month visit and isradipine CL/F ($r_s$=0.18, p-value=0.035). This correlation was stronger in men ($r_s$=0.24, p-value=0.015), but not significant in women ($r_s$=−0.24, p-value=0.16). A linear regression model also revealed CL/F of isradipine to be an independent predictor of cumulative levodopa equivalent dose (LED) over 36 months (β coefficient=0.47; p-value=0.01); that is, cumulative LED would increase by approximately 5-mg for every 10 L/h increase in plasma CL/F of isradipine.

These results indicate that higher exposure to isradipine, with correspondingly higher Cave and Cmin, and greater time above threshold, can delay the progression of PD, as determined by a delay in the need for symptomatic PD medication. In addition, higher isradipine exposure was associated with requiring a lower dose of symptomatic therapy (levodopa). Thus, maintaining consistently high plasma concentrations for the majority of the 24-hour day— as determined by higher Cmin, higher Cave, and longer time above threshold—was associated with better outcome.

Example 4—Preparation of an Extended Release Isradipine Tablet

An osmotic dosage form is prepared as follows:
  a) A drug containing composition is prepared by passing through a 40 mesh screen 261.7 g polyethylene oxide having a molecular weight of about 200,000. Then 6.82 g isradipine and 30 g hydroxypropylmethylcellulose having a number average molecular weight of 11,200 is added to the polyethylene oxide and the ingredients are mixed for about 10 minutes in a conventional mixer. While the ingredients are mixing, 300 ml denatured, anhydrous ethanol is slowly added to the mixer and the mixing is continued for an additional 5 minutes.
  b) The wet granulation is passed through a 20 mesh screen then dried at room temperature for 16 hours and passed again through the 20 mesh screen.
  c) Subsequently, 1.5 g magnesium stearate is added to the granulation and the composition is mixed in a roller mill for 1 to 3 minutes.
  d) A second composition is prepared by mixing 194.5 g of polyethylene oxide having a molecular weight of 7,500,500 with 72 g of sodium chloride. The homogenous blend is then passed through a 40 mesh screen and mixed with 30 g hydroxypropylmethylcellulose having a number average molecular weight of 11,200 and 3 g of ferric oxide for 10 minutes in a mixer. Then, 300 ml of denatured, anhydrous ethanol is slowly added while continuing the mixing for an additional 5 minutes.
  e) The second wet granulation just prepared is passed through a 20 mesh screen, allowed to dry at room temperature for 16 hours, and again passed through a 20 mesh screen.
  f) Subsequently, 1.5 g magnesium stearate is added to the second granulation and the composition is mixed in a roller mill for 1 to 3 minutes.

g) A tablet press is used to form a laminate. First, 220 mg of the composition comprising the drug is added to the press and tamped; then, 130 mg of the second granulated material prepared above is added to the press and the two materials are pressed into a laminated core. This lamination is repeated to produce 1200 laminated cores.

h) A coating solution is prepared containing 9.7 g cellulose acetate having an acetyl content of 39.8%, 0.3 g polyethylene glycol, 240 g methylene chloride:methanol (90:10 wt:wt).

i) The coating solution is sprayed onto the laminated cores using a fluidized bed coater and the coated cores are dried in the fluidized bed coater for 15 minutes then air dried at room temperature for 24 hours.

j) Finally, a 0.635 mm exit orifice is laser drilled on the drug laminate side of the osmotic device and residual solvent is removed by further drying at 50 C, 50% RH for 48 hours followed by 50 C for 1 hour to remove any excess moisture.

k) Each of the osmotic dosage forms prepared contains 5.0 mg isradipine.

We claim:

1. A method of slowing progression of Parkinson's disease in a patient comprising:
   (i) administering to said patient a pharmaceutical composition,
      wherein said pharmaceutical composition comprises isradipine,
      wherein the daily dose of isradipine for said patient is 3 mg to 15 mg,
      wherein administration of said pharmaceutical composition to a patient provides a mean plasma profile for isradipine at steady state characterized by a Css of 1.5 to 3.5 ng/ml for not less than 12 hours over a 24 hour period; and
   (ii) monitoring the steady state plasma concentration of isradipine in the patients for a period of at least four weeks.

2. A method of treating a patient diagnosed with Parkinson's disease comprising:
   (i) administering to said patient a pharmaceutical composition,
      wherein said pharmaceutical composition comprises isradipine,
      wherein the daily dose of isradipine for said patient is 3 mg to 12 mg,
      wherein administration of said pharmaceutical composition to a patient provides a mean plasma profile for isradipine at steady state characterized by a Css of 2.0 to 3.5 ng/ml for not less than 12 hours over a 24-hour period; and
   (ii) monitoring the steady state plasma concentration of isradipine in the patients for a period of at least four weeks.

3. A method of delaying the onset of dopaminergic therapy in a patient with Parkinson's disease comprising:
   (i) administering to said patient a pharmaceutical composition,
      wherein said pharmaceutical composition comprises isradipine,
      wherein the daily dose of isradipine for said patient is 3 mg to 15 mg,
      wherein administration of said pharmaceutical composition to a patient provides a mean plasma profile for isradipine at steady state characterized by a Css of 1.5 to 3.5 ng/ml for not less than 12 hours over a 24 hour period; and
   (ii) monitoring the steady state plasma concentration of isradipine in the patients for a period of at least four weeks.

4. A method of treating a patient diagnosed with Parkinson's disease comprising:
   (i) administering to said patient a pharmaceutical composition,
      wherein said pharmaceutical composition comprises isradipine,
      wherein the daily dose of isradipine for said patient is 3 mg to 15 mg,
      wherein administration of said pharmaceutical composition to a patient provides a mean plasma profile for isradipine at steady state characterized by a Css of 1.5 to 3.5 ng/ml for not less than 12 hours over a 24 hour period; and
   (ii) further comprising the step of monitoring the steady state plasma concentration of isradipine in the patients for a period of at least four weeks.

5. The method of claim 4, wherein administration of said pharmaceutical composition to a patient provides a mean plasma profile for isradipine at steady state characterized by a Css of 1.5 to 3.5 ng/ml for not less than 16 hours over a 24 hour period.

6. The method of claim 4, wherein administration of said pharmaceutical composition to a patient provides a mean plasma profile for isradipine at steady state characterized by a Css of 1.5 to 3.5 ng/ml for not less than 20 hours over a 24 hour period.

7. The method of claim 4, wherein administration of said pharmaceutical composition to a patient provides a mean plasma profile for isradipine at steady state characterized by a Css of 2.0 to 3.5 ng/ml for not less than 12 hours over a 24 hour period.

8. The method of claim 4, wherein administration of said pharmaceutical composition to a patient provides a mean plasma profile for isradipine at steady state characterized by a Css of 2.0 to 3.5 ng/ml for not less than 16 hours over a 24 hour period.

9. The method of claim 4, wherein administration of said pharmaceutical composition to a patient provides a mean plasma profile for isradipine at steady state characterized by a Css of 2.0 to 3.5 ng/ml for not less than 20 hours over a 24 hour period.

10. The method of claim 4, wherein administration of said pharmaceutical composition to a patient provides a mean plasma profile for isradipine at steady state characterized by a fluctuation less than 100%.

11. The method of claim 4, wherein administration of said pharmaceutical composition to a patient provides a mean plasma profile for isradipine at steady state characterized by a fluctuation less than 70%.

12. The method of claim 11, wherein said pharmaceutical composition is administered once daily.

13. The method of claim 11, wherein said pharmaceutical composition is administered twice daily.

14. The method of claim 4, wherein said pharmaceutical composition is administered orally.

15. The method of claim 4, wherein said pharmaceutical composition is administered parenterally.

16. The method of claim 4, wherein said daily dose is 6 to 16 mg.

17. The method of claim 4, wherein said daily dose is 9 to 16 mg.

18. The method of claim 4, wherein said daily dose is 9 to 15 mg.

19. The method of claim 4, wherein said daily dose is 10 mg.

20. The method of claim 4, wherein said pharmaceutical composition comprises 3 mg to 15 mg isradipine.

21. The method of claim 4, wherein said pharmaceutical composition comprises 3 mg to 12 mg isradipine.

22. The method of claim 4, wherein said pharmaceutical composition comprises 3 mg to 10 mg isradipine.

23. The method of claim 4, wherein said pharmaceutical composition comprises 5 mg to 10 mg isradipine.

\* \* \* \* \*